(12) United States Patent
Adamczyk (10) Patent No.: US 10,736,581 B2
(45) Date of Patent: *Aug. 11, 2020

(54) MONITORING OF HEALTH (71) Applicant: AT&T Intellectual Property I, L.P., Atlanta, GA (US)

(72) Inventor: Maria Adamczyk, Atlanta, GA (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 1020 days.

This patent is subject to a terminal disclaimer.

(21) Appl. No.: 14/316,858

(22) Filed: Jun. 27, 2014

(65) Prior Publication Data

US 2014/0310022 A1   Oct. 16, 2014

Related U.S. Application Data (63) Continuation of application No. 11/805,927, filed on May 25, 2007, now Pat. No. 8,795,171, which is a continuation of application No. 10/631,549, filed on Jul. 31, 2003, now Pat. No. 7,238,156.

(51) Int. Cl.
*A61B 5/00* (2006.01)
*G06F 19/00* (2018.01)
*G06Q 50/22* (2018.01)
*H04L 29/06* (2006.01)
*H04W 8/20* (2009.01)

(52) U.S. Cl.
CPC ........ *A61B 5/7282* (2013.01); *G06F 19/3418* (2013.01); *G06Q 50/22* (2013.01); *H04L 67/42* (2013.01); *H04W 8/20* (2013.01); *G06F 2212/174* (2013.01); *Y10S 128/904* (2013.01); *Y10S 128/92* (2013.01)

(58) Field of Classification Search
CPC ................ A61B 5/00; G16H 50/00–80; G08B 21/00–0211
USPC ............... 600/340; 340/539.11–539.12, 540; 340/573.1–573.7; 702/19, 189–194; 703/11; 705/2–3
See application file for complete search history.

(56) References Cited

U.S. PATENT DOCUMENTS

| | | |
|---|---|---|
| 4,760,593 A | 7/1988 | Shapiro et al. |
| 4,838,275 A | 6/1989 | Lee |
| 4,918,717 A | 4/1990 | Bissonnette et al. |
| 5,262,944 A | 11/1993 | Weisner et al. |
| 5,333,171 A | 7/1994 | Wang et al. |
| 5,343,869 A | 9/1994 | Pross et al. |

(Continued)

OTHER PUBLICATIONS

Unknown, "Samsung integrate digital camera and phone," Jun. 23, 2000, 2 pages.

(Continued)

*Primary Examiner* — Gary Jackson
*Assistant Examiner* — Jonathan T Juo
(74) *Attorney, Agent, or Firm* — Scott P. Zimmerman, PLLC (57) ABSTRACT

A health monitoring system receives a health condition reading from a mobile device. The health condition reading is compared to ranges of data defining acceptable health conditions. If the health condition reading lies outside one of the ranges of data, then an alert may be generated and sent to the mobile device. The alert informs a user that the health condition reading is unacceptable, perhaps requiring medical attention.

20 Claims, 5 Drawing Sheets

(56) References Cited

U.S. PATENT DOCUMENTS

| | | | |
|---|---|---|---|
| 5,348,008 A | 9/1994 | Bornn et al. | |
| 5,416,695 A * | 5/1995 | Stutman | A61B 5/1112 |
| | | | 379/38 |
| 5,438,568 A | 8/1995 | Weisser, Jr. | |
| 5,553,609 A | 9/1996 | Chen et al. | |
| 5,589,818 A | 12/1996 | Queen | |
| 5,717,379 A | 2/1998 | Peters | |
| 5,724,025 A | 3/1998 | Tavori | |
| 5,797,838 A | 8/1998 | Oka | |
| 5,812,054 A | 9/1998 | Cohen | |
| 5,884,032 A | 3/1999 | Bateman et al. | |
| 5,889,474 A * | 3/1999 | LaDue | G07C 9/00111 |
| | | | 340/10.41 |
| 6,094,134 A | 7/2000 | Cohen | |
| 6,138,026 A * | 10/2000 | Irvin | G01S 5/0027 |
| | | | 455/456.3 |
| 6,174,283 B1 | 1/2001 | Nevo et al. | |
| 6,271,752 B1 | 8/2001 | Valos | |
| 6,292,542 B1 | 9/2001 | Bilder | |
| 6,295,346 B1 | 9/2001 | Markowitz et al. | |
| 6,302,844 B1 * | 10/2001 | Walker | A61B 5/1112 |
| | | | 128/904 |
| 6,330,499 B1 | 12/2001 | Chou et al. | |
| 6,356,841 B1 | 3/2002 | Hamrick et al. | |
| 6,383,136 B1 | 5/2002 | Jordan | |
| 6,398,727 B1 | 6/2002 | Bui et al. | |
| 6,442,241 B1 | 8/2002 | Tsumpes | |
| 6,443,890 B1 | 9/2002 | Schulze et al. | |
| 6,445,300 B1 | 9/2002 | Luman | |
| 6,454,708 B1 | 9/2002 | Ferguson et al. | |
| 6,471,087 B1 | 10/2002 | Shusterman | |
| 6,478,736 B1 | 11/2002 | Mault | |
| 6,485,415 B1 | 11/2002 | Uchiyama et al. | |
| 6,504,909 B1 | 1/2003 | Cook et al. | |
| 6,519,241 B1 | 2/2003 | Theimer | |
| 6,553,106 B1 | 4/2003 | Gould et al. | |
| 6,563,910 B2 | 5/2003 | Menard et al. | |
| 6,567,502 B2 | 5/2003 | Zellner et al. | |
| 6,602,191 B2 | 8/2003 | Quy | |
| 6,618,588 B1 * | 9/2003 | Easley | H04M 3/42042 |
| | | | 379/88.19 |
| 6,748,052 B2 | 6/2004 | Zellner et al. | |
| 6,758,812 B2 | 7/2004 | Lang | |
| 6,775,670 B2 * | 8/2004 | Bessette | G06F 19/322 |
| 6,804,558 B2 | 10/2004 | Haller et al. | |
| 6,807,564 B1 | 10/2004 | Zellner et al. | |
| 6,812,840 B2 | 11/2004 | Gehlot et al. | |
| 6,819,247 B2 | 11/2004 | Birnbach et al. | |
| 6,858,006 B2 | 2/2005 | MacCarter et al. | |
| 6,893,396 B2 | 5/2005 | Schulze et al. | |
| 6,897,788 B2 | 5/2005 | Khair et al. | |
| 6,936,007 B2 | 8/2005 | Quy | |
| 6,963,579 B2 * | 11/2005 | Suri | H04L 12/2856 |
| | | | 370/420 |
| 6,982,639 B2 | 1/2006 | Brackett et al. | |
| 7,081,091 B2 | 7/2006 | Merrett et al. | |
| 7,120,488 B2 | 10/2006 | Nova et al. | |
| 7,222,054 B2 | 5/2007 | Geva | |
| 7,237,205 B2 | 6/2007 | Sarel | |
| 7,319,780 B2 | 1/2008 | Fedorovskaya et al. | |
| 7,395,117 B2 | 7/2008 | Mazar et al. | |
| 7,448,996 B2 | 11/2008 | Khanuja et al. | |
| 7,689,438 B1 * | 3/2010 | Rappaport | G06Q 30/02 |
| | | | 600/300 |
| 7,905,832 B1 | 3/2011 | Lau et al. | |
| 8,055,509 B1 | 11/2011 | Walker et al. | |
| 9,135,236 B2 * | 9/2015 | Syri | G06F 17/2715 |
| 2002/0027975 A1 | 3/2002 | Oxley | |
| 2003/0091159 A1 | 5/2003 | Oxley | |
| 2003/0112804 A1 * | 6/2003 | Kamarainen | H04H 20/08 |
| | | | 370/390 |
| 2003/0120135 A1* | 6/2003 | Gopinathan | A61B 5/411 |
| | | | 600/300 |
| 2003/0225315 A1 | 12/2003 | Merrett et al. | |
| 2004/0183695 A1 | 9/2004 | Ruokangas et al. | |
| 2005/0059870 A1 * | 3/2005 | Aceti | A61B 5/0002 |
| | | | 600/340 |
| 2005/0075542 A1 * | 4/2005 | Goldreich | A61B 5/0205 |
| | | | 600/300 |

OTHER PUBLICATIONS

Daniel L. Lough et al., "A Short Tutorial on Wireless LANS and IEEE 802.11," retrieved from http://computer.org/students/looking/summer97/ieee802.htm on Sep. 7, 2000, 5 pages.

Description of ITI Wireless Intrusion Sensors, pp. 1-3, available on Feb. 22, 2000.

* cited by examiner

MONITORING OF HEALTH

CROSS-REFERENCE TO RELATED APPLICATIONS

This application is a continuation of U.S. patent application Ser. No. 11/805,927 filed May 25, 2007 and since issued as U.S. Pat. No. 8,795,171, which is a continuation of U.S. patent application Ser. No. 10/631,549 filed Jul. 31, 2003 and since issued as U.S. Pat. No. 7,238,156, with both applications incorporated herein by reference in their entireties.

BACKGROUND

In the medical industry, it is common practice to utilize instruments and devices to monitor the health condition of patients. The health condition of a patient may be defined by measuring and recording a quantifiable parameter such as, for example, pulse, blood pressure, blood sugar, and cholesterol and then comparing the recorded measurement against a predefined range that a physician may establish for each patient. If the recorded measurement is within the predefined range, the patient's health may be considered satisfactory. In contrast, a recorded measurement that falls outside the predefined range may cause a physician to further explore the nonconforming reading and ultimately prescribe medical treatment.

Generally, the instruments and devices that are capable of monitoring a patient's health are located at doctors' offices, hospitals, or other medical facilities, and thus require patients to travel from their residence or workplace to monitor their particular health condition(s). However, many people such as, for example, elderly individuals, have health conditions that necessitate constant monitoring. In addition, the inconvenience and expense of doctor/hospital visits may also prevent individuals from monitoring their particular condition and thus prevent such individuals from maintaining good health.

SUMMARY

In one general respect, one embodiment of the present invention is directed to a health monitoring system. According to this embodiment, the health monitoring system includes a first server configured to receive a first set of information from a monitoring device, wherein the first set of information includes a health condition reading of a subscriber, and wherein the first server is configured to process the first set of information and transmit a second set of information to the monitoring device and/or a telecommunications device, wherein the second set of information includes medical treatment information and/or medical advice concerning the subscriber. The health monitoring system also includes a database in communication with the first server and configured to store a third set of information therein, wherein the third set of information includes emergency contact information, one or more health conditions of the subscriber, monitoring time intervals, and/or numerical ranges defining acceptable health conditions and medical alert conditions.

BRIEF DESCRIPTION OF THE DRAWINGS

Further advantages of the present invention may be better understood by referring to the following description taken in conjunction with the accompanying drawings, in which.

DESCRIPTION

It is to be understood that the figures and descriptions of the present invention have been simplified to illustrate elements that are relevant for a clear understanding of the present invention, while eliminating, for purposes of clarity, other elements of a conventional telecommunications network. For example, certain operating system details and modules of certain of the intelligent platforms of the network are not described herein. Those of ordinary skill in the art will recognize, however, that these and other elements may be desirable in a typical telecommunications network. However, because such elements are well known in the art and because they do not facilitate a better understanding of the present invention, a discussion of such elements is not provided herein.

The term "calling party" is used herein generally to refer to the person or device that initiates a telecommunication. In some cases, the calling party may not be a person, but may be a device such as a facsimile machine, an answering service, a modem, etc. The term "communication" is used herein to include all messages or calls that may be exchanged between a calling party and a called party, including, but not limited to, voice, data and video messages. The term "communication" is used synonymously herein with the term "call" unless a distinction is noted. The term "subscriber" is used herein to generally refer to a subscriber of the described telecommunications service. The subscriber may also be referred to herein as "patient" or as "subscribing patient."

According to one embodiment, the system of the present invention utilizes the intelligent functionality of an Advanced Intelligent Network (AIN). The AIN is a network that may be used in conjunction with a conventional telephone network, such as the public switched telephone network (PSTN), to provide enhanced voice and data services and dynamic routing capabilities using two different networks. The actual voice call is transmitted over a circuit-switched network, but the signaling is done on a separate packet-switched network. In another embodiment, the AIN may be a service independent architecture designed to be programmable and controlled by software distributed in elements throughout the network. In addition, the AIN may reside in a Common Channel Signaling (CCS) network, using Signaling System 7 (SS7) protocol to request routing instruction. Before describing details of the system of the present invention, a description of the AIN is provided.

Figure 1:
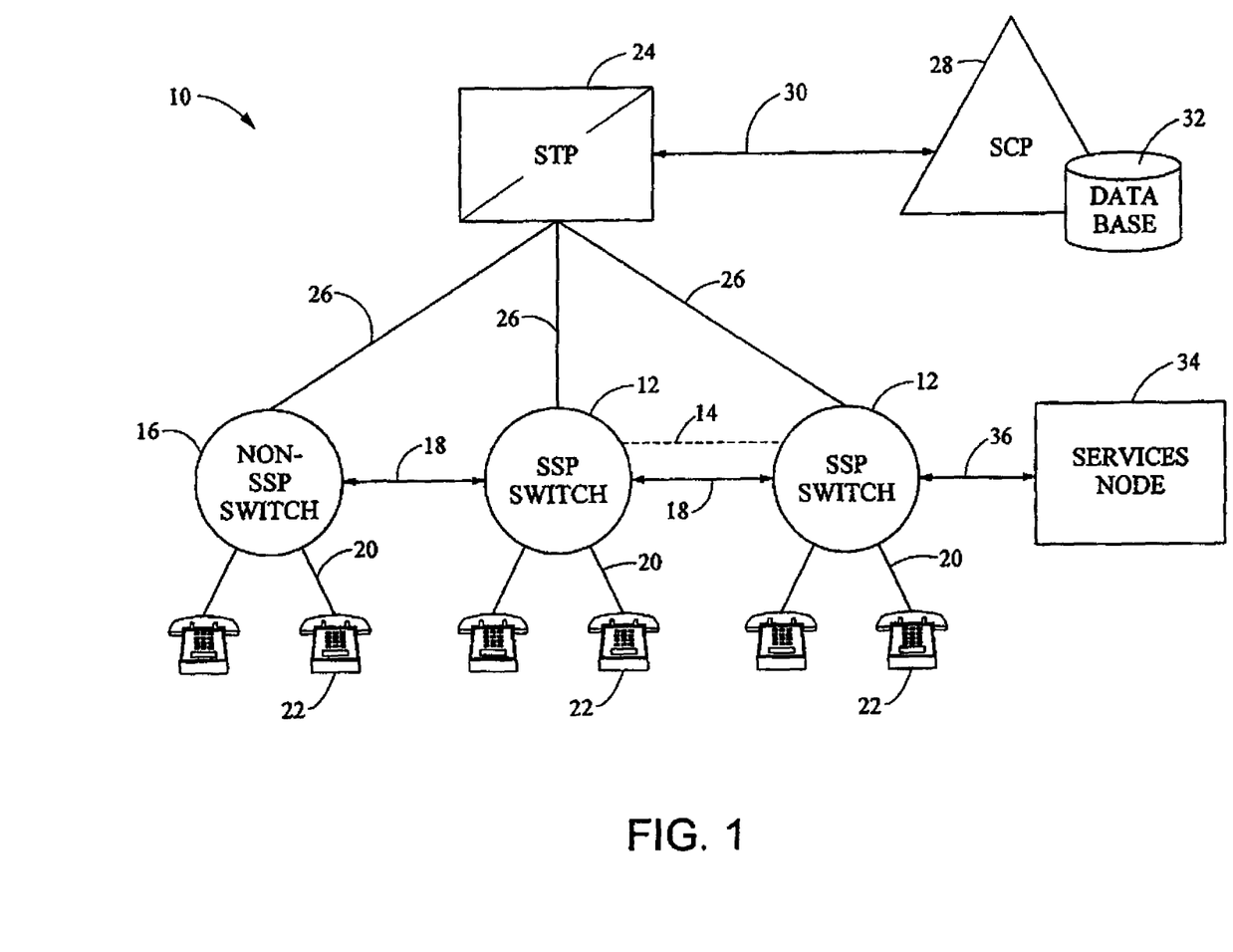
FIG. 1 is a block diagram of an Advanced Intelligent Network (AIN) for integration with a public switched telephone network according to one embodiment of the present invention.

FIG. 1 is a block diagram of an Advanced Intelligent Network (AIN) 10 for integration with the public switched telephone network (PSTN) according to one embodiment of the present invention. The AIN 10 may be employed by a Local Exchange Carrier (LEC) and may be utilized by the LEC to allow the LEC to provide call processing features and services that are not embedded within conventional switching circuits of the PSTN.

A typical LEC includes a number of central office (CO) switches for interconnecting customer premises terminating equipment with the PSTN. For an LEC including the AIN 10 as illustrated in FIG. 1, the central office switches may be provided as Service Switching Points (SSP) switches 12. The dashed line 14 between the SSP switches 12 indicates that the number of SSP switches 12 in the AIN 10 may vary depending on the particular requirements of the AIN 10. The AIN 10 may also include a non-SSP switch 16. The difference between the SSP switches 12 and the non-SSP switch 16 is that the SSP switches 12 provide intelligent network functionality. Interconnecting the SSP switches 12 and the non-SSP switch 16 are communication links 18 which maybe, for example, trunk circuits.

Each SSP switch 12 and non-SSP switch 16 has a number of subscriber lines 20 connected thereto. The subscriber lines 20 may be, for example, conventional twisted pair loop circuits (i.e. Plain Old Telephone Service (POTS)) connected between the switches 12, 16 and the telephone drops for the customer premises, or the subscriber lines 20 may be trunk circuits, such as T-1 trunk circuits, a Digital Subscriber Line (DSL), or an Integrated Services Digital Network (ISDN). The number of subscriber lines 20 connected to each switch 12 and switch 16 may be on the order of, for example, ten thousand to one hundred thousand lines. Each of the subscriber lines 20 is connected to a terminating piece of customer premises equipment, represented in FIG. 1 by the landline telephones 22. Alternatively, the terminating equipment may be other types of telecommunications devices such as, for example, a telecopier, a personal computer, a modem, or a private branch exchange (PBX) switching system.

For the AIN 10 illustrated in FIG. 1, each SSP switch 12 and the non-SSP switch 16 are connected to a signal transfer point (STP) 24 via a communication link 26. The communication link 26 may employ, for example, the SS7 switching protocol. The STP 24 may be a multi-port high speed packet switch that is programmed to respond to the routing information in the appropriate layer of the switching protocol and route the data packets to their intended destination.

One of the intended destinations of the data packets from the STP 24 is a service control point (SCP) 28. The STP 24 is in communication with the SCP 28 via a communication link 30, which may also employ the SS7 switching protocol. The SCP 28 may be an intelligent database server such as, for example, an Intelligent Network Service Control Point available from Lucent Technologies Inc., Murray Hill, N.J., and may have associated with it a network database 32 for storing network data. The intelligent functionality of the SCP 28 may be realized by application programs, such as programmable Service Program Applications (SPA), which are run by the SCP 28. The SCP 28 may be employed to implement high volume routing services, such as call forwarding and number portability translation and routing. In addition, another of the functions of the SCP 28 is hosting of the network database 32, which may store subscriber information, such as subscriber call management profiles, used in providing enhanced calling services.

The AIN 10 illustrated in FIG. 1 also includes a services node (SN) 34. The SN 34 may be, for example, a Compact Services Node (CSN) available from Lucent Technologies Inc., Murray Hill, N.J., although the SN 34 may be any other type of available intelligent peripheral. The SN 34 may be connected to one or more of the SSP switches 12 via a communications link 36 which may be, for example, an Integrated Service Digital Network (ISDN), including BRI (Basic Rate Interface) or PRI (Primary Rate Interface) lines. According to other embodiments, the communications link 36 may be, for example, a T-1 trunk circuit.

In order to keep the processing of data and calls as simple as possible at the switches, such as at the SSP switches 12, a set of triggers may be defined at the SSP switches 12 for each call. A trigger in an AIN is an event associated with a particular subscriber line 20 that generates a data packet to be sent from the SSP switch 12 servicing the particular subscriber line 20 to the SCP 28 via the STP 24. The triggers may be originating triggers for calls originating from the subscriber premises or terminating triggers for calls terminating at the subscriber premises. A trigger causes a message in the form of a query to be sent from the SSP switch 12 to the SCP 28.

The SCP 28 in turn interrogates the database 32 to determine whether some customized call feature or enhanced service should be implemented for the particular call or whether conventional dial-up telephone service should be provided. The results of the database inquiry are sent back from the SCP 28 to the SSP switch 12 via the STP 24. The return packet includes instructions to the SSP switch 12 as to how to process the call. The instructions may be to take some special action as a result of a customized calling service or enhanced feature. For example, for an enhanced calling feature requiring the capabilities of the SN 34, the return message from the SCP 28 may include instructions for the SSP switch 12 to route the call to the SN 34. In addition, the return message from the SCP 28 may simply be an indication that there is no entry in the database 32 that indicates anything other than conventional telephone service should be provided for the call. The query and return messages may be formatted, for example, according to conventional SS7 TCAP (Transaction Capabilities Application Part) formats. U.S. Pat. No. 5,438,568, which is incorporated herein by reference, discloses additional details regarding the functioning of an AIN.

The AIN 10 illustrated in FIG. 1 includes only one STP 24, one SCP 28, one network database 32, and one SN 34, although the AIN 10 may further include an additional number of these components as well as other network components which are not included in FIG. 1 for purposes of clarity. For example, the AIN 10 may additionally include redundant SCPs and STPs to take over if the STP 24 or the SCP 28 should fail. In addition, the AIN 10 may include an Automatic Electronic Switching System (AESS) Network Access Point (NAP) in communication with the STP 24, which may be programmed to detect the trigger conditions. Further, the AIN 10 may include regional STPs and regional SCPs in communication with, for example, the local STP 24, for routing and servicing calls between different LECs.

Figure 2:
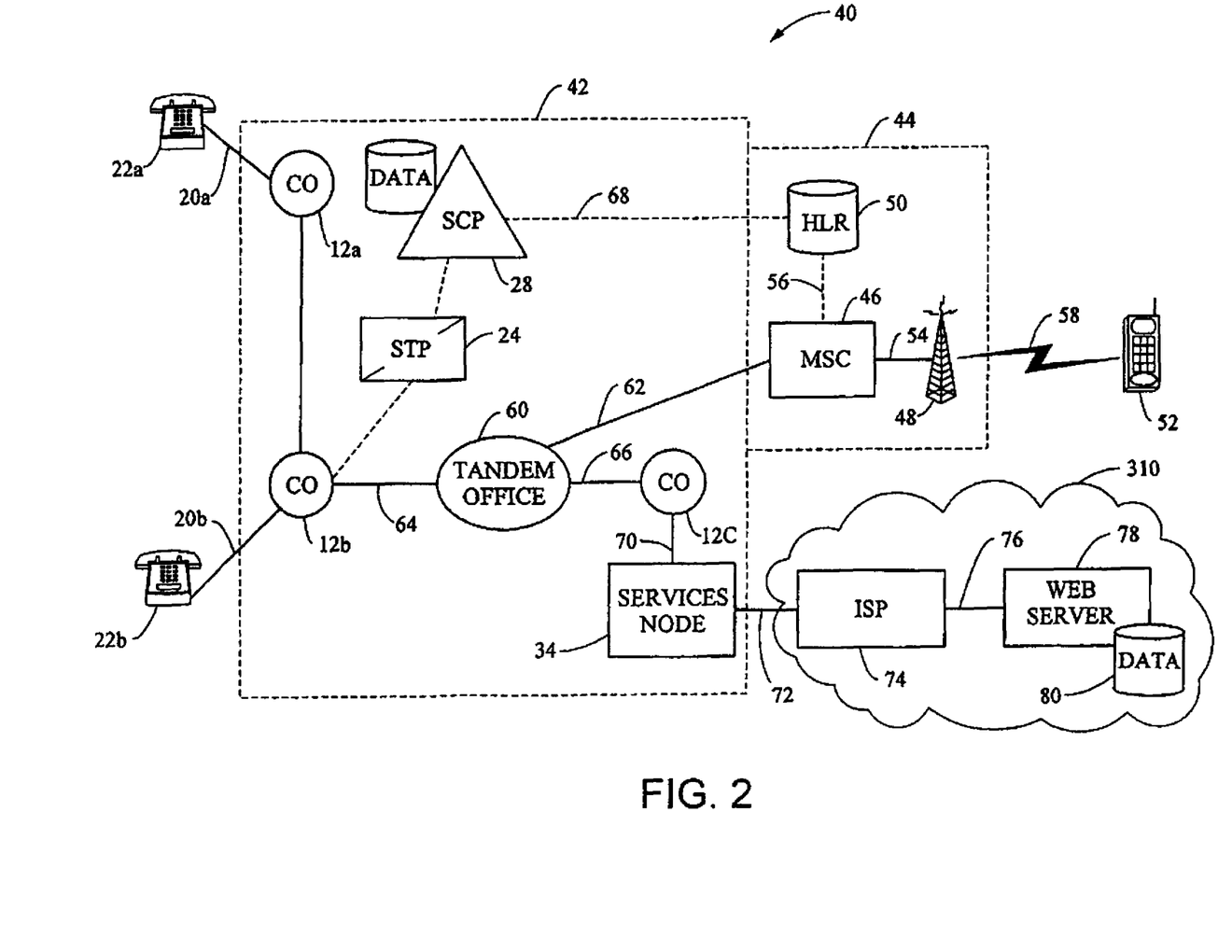
FIG. 2 is a block diagram of a system according to one embodiment of the present invention.

The present invention is directed, according to one embodiment, to a system for monitoring the health condition (s) of a patient such as, for example, pulse, blood pressure, blood sugar, and cholesterol. FIG. 2 is a diagram of a system 40 according to one such embodiment. For clarity, the communications links shown in FIG. 2 that are used exclusively for signaling (e.g., no call data) are illustrated with dashed lines, and communications links that transfer signaling or call data are illustrated with solid lines. The system 40 includes a landline network 42 and a wireless network 44. The landline network 42 includes portions of an AIN as described in conjunction with FIG. 1, including the CO SSP switches 12*a*-*c* (designated as "CO" in FIG. 2 and referred to as "CO switch(es)" hereinafter), the STP 24, the SCP 28, and the SN 34. The landline telephones 22*a*, 22*b* are in communication with the switches 12*a*, 12*b* via subscriber lines 20a, 20b, respectively. For purposes of clarity, other elements of an AIN are not shown in FIG. 2.

The wireless network 44 includes a mobile switching center (MSC) 46, a base transceiver station (BTS) 48, and a home location register (HLR) 50. The MSC 46 is in communication with a wireless telecommunications device 52, such as a wireless telephone, as illustrated in FIG. 2, via the BTS 48. The BTS 48 may communicate with wireless telecommunications device 52 according to an air-interface communication scheme 58 such as, for example, AMPS (ANSI-553), TDMA (IS-136), CDMA (IS-95), or GSM. The BTS 48 may be in communication with the MSC 46 via the communications link 54. The MSC 46 is an automatic switching system in a wireless telecommunications network that acts as the interface for subscriber traffic between the wireless network 44 and the landline network 42 or other MSCs in the same or other wireless networks. The MSC 46 performs the same general function as a central office switch in a landline based system. In addition, the MSC 46 supports incoming calls through a radio telecommunications front-end, as well as handoff and roaming functions. Accordingly, the MSC 46 may include wireless IN functionality for detecting originating and terminating triggers (e.g. WIN and CAMEL).

The MSC 46 may be in communication with the HLR 50 via a communications link 56 which may, for example, be an SS7 signaling protocol link. The HLR 50 is a location register to which the user identity of a wireless telecommunications device, such as the wireless telephone 52, is assigned for record purposes. The HLR 50 may register subscriber information relating to wireless telecommunications devices such as, for example, profile information, current location, and authorization period. When the MSC 46 detects a wireless telecommunications device entering the MSC's service area, the MSC 46 performs a registration process that includes requesting subscriber profile information from either the HLR 50 or a visitor location register (VLR) (not shown), depending upon whether the wireless telephone 52 is within its home location or within a visitor location. For integrated wireless networks, the VLR assigned to the service area of a visiting wireless subscriber may be updated with information from the HLR associated with the wireless subscriber's wireless service provider (WSP). Accordingly, the MSC 46 servicing a particular area has access to information regarding each of the wireless users presently in its service area. In addition, the HLR 50 of the wireless network 44 may be in communication with the SCP 28 of the landline network 42, via a communications link 68 employing, for example, the IS-41 signaling protocol.

The landline network 42 additionally includes a tandem office 60, which provides a switching interface between the landline network 42 and the wireless network 44. The tandem office 60 may be in communication with the MSC 46 via a communications link 62, which may be, for example, a trunk circuit or an ISDN. In addition, the tandem office 60 may be in communication with the CO switches (such as CO switches 12b, 12c as illustrated in FIG. 2) via communications links 64, 66 respectively, which may be, for example, trunk circuits.

Also, the CO switches (such as the CO switch 12c, as illustrated in FIG. 2). may be in communication with a services node (SN) 34 via a communications link 70, which may be, for example, an Integrated Service Digital Network (ISDN), including BRI (Basic Rate Interface) or PRI (Primary Rate Interface) lines. According to other embodiments, the communications link 70 may be, for example, a T-1 trunk circuit.

In one embodiment of the present invention, the SN 34 executes programmable applications to access a server 78, such as, for example, a web server, to provide either the wireless device 52 or the landline device 22a, 22b with call specific information. The SN 34 then transmits such information to the wireless network 44 or the landline network 42, via the tandem office 60. In one embodiment of the present invention, the SN 34 may function as a voice/web gateway to allow the landline network 42 to access a network 310, such as, for example, the Internet and an Internet service provider 74 via a communications link 72, which may be, for example, a TCP/IP (Transmission Control Protocol/Internet Protocol) connection. Also, the Internet service provider 74 may be in communication with the server 78 and its corresponding database 80, via a communications link 76, which may be, for example, another TCP/IP connection. In another embodiment, the SN 34 may be located in the wireless network 44.

In one embodiment, where the personal health monitoring service is provided as a subscriber service by a telecommunications provider, the SN 34 may execute programmable applications to access the server database 80 to provide, for example, audio, video, graphics, and/or text files that include medical treatment information and/or medical advice concerning the subscriber's health condition.

Figure 3:
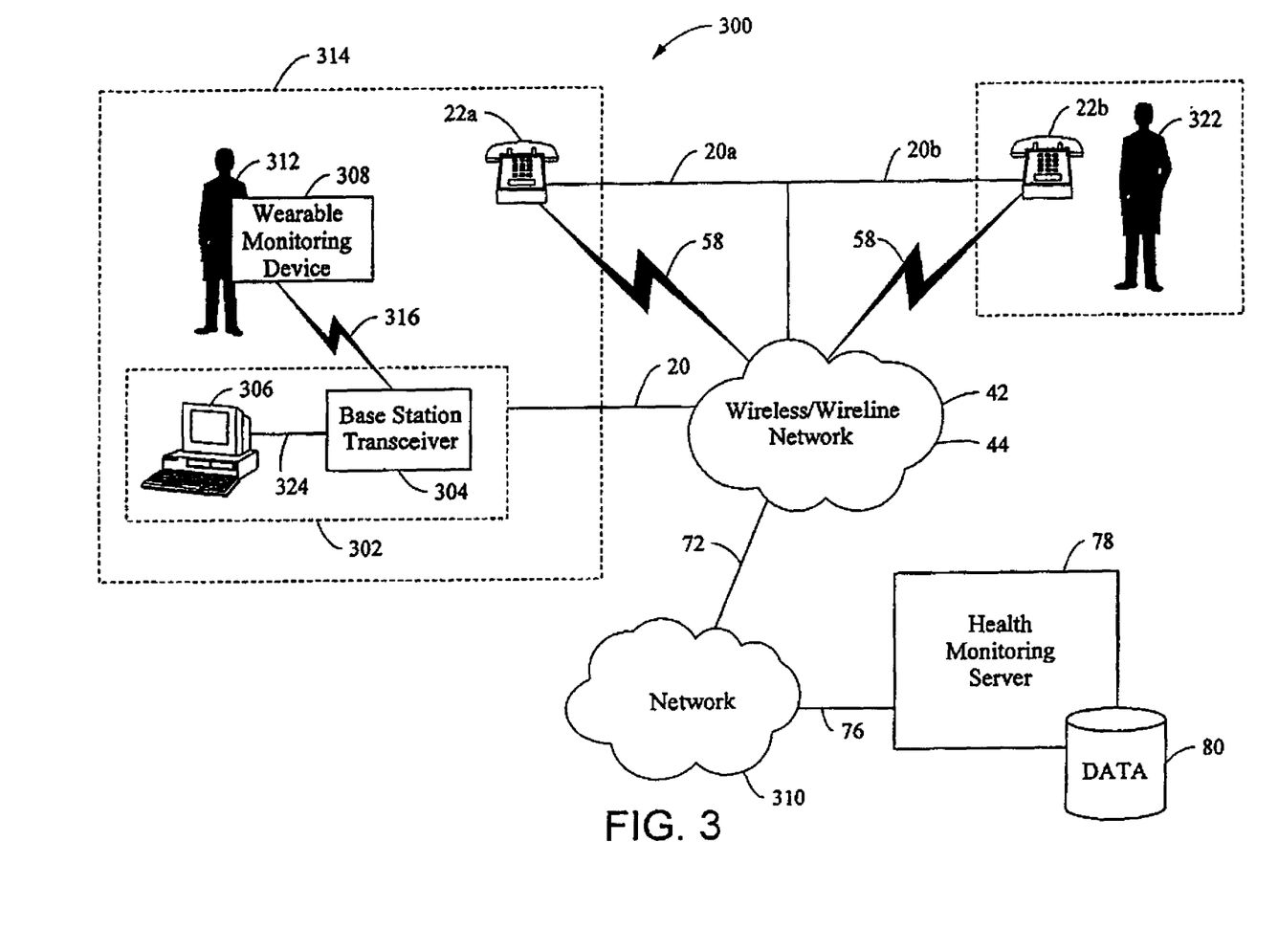
FIG. 3 is a block diagram of a system according to another embodiment of the present invention.

FIG. 3 is a block diagram of a system 300 according to one embodiment of the present invention. According to this embodiment, a local server 302 may be located, for example, at a subscriber's 312 residence or workplace 314. The local server 302 may include, for example, a personal computer 306 that provides network addressing and routing and functions as a gateway between the home/workplace 314 and a network 310 such as, for example, the Internet. In addition, the local server 302 may, for example, also include one or more base station transceivers 304 that are configured to transmit and receive signals to and from a monitoring device 308 that may be worn by the subscriber 312. In one embodiment, the subscriber 312 may, for example, wear the monitoring device 308 around his/her wrist or neck similar to a wristwatch or necklace. In another embodiment, the subscriber 312 may attach the monitoring device 308 to his/her clothing such as, for example, attaching the monitoring device 308 to his/her belt, sock, pants or shirt.

According to one embodiment of the present invention, a signal 316 received by the base station transceiver 304 from the monitoring device 308 may, for example, include data regarding pulse, blood pressure, blood sugar level or any other parameter that a. physician may establish for the subscriber 312 such as, for example, an electrocardiogram. According to this embodiment, the base station transceiver 304 may, for example, be coupled to the personal computer 306 via a wire or wireless communications link 324. The personal computer 306 may, therefore, receive the data from the base station transceiver 304 and process, store, and/or relay the data to a server 78, which may be configured as a health monitoring server, via a dialup or permanent connection to the network 310.

In one embodiment, the communications link 324 may be a wired connection such as, for example, conventional twisted pair copper wire or a coaxial cable connection. Alternatively, communications link 324 may be implemented as a wireless connection such as, for example, IEEE 802.11 wireless LAN or Bluetooth technologies.

In another embodiment, the system 300 may include a communications link 20 that may be conventional twisted pair loop circuits (i.e. Plain Old Telephone Service (POTS)), trunk circuits, such as T-1 trunk circuits, a Digital Subscriber Line (DSL), or an Integrated Services Digital Network (ISDN). In addition, a service node 34 (not shown) included in the wireless/wireline network 42, 44 may function as a voice/web gateway to allow the wireless/wireline network 42, 44 to access an Internet service provider (not shown) via a communications link 72, which may be, for example, a TCP/IP (Transmission Control Protocol/Internet Protocol) connection.

In one embodiment, the Internet service provider may, for example, be in communication with the server 78 via a communications link 76, which may be, for example, another TCP/IP connection. According to this embodiment, the server 78 may include a database 80 that is configured to store numerical ranges that identify acceptable and unacceptable health condition(s) for the subscriber 312. In another embodiment, the server 78 may also be configured to compare the predefined ranges with the current health condition readings obtained from the monitoring device 308.

In yet another embodiment, the personal computer 306 may receive information from the server 78, via communications link 20. According to this embodiment, the personal computer 306 may relay such information to the base station transceiver 304 which may in turn transmit the signal 316 to the monitoring device 308. In one embodiment, the signal 316 may include data such as, for example, text messages involving medical instructions that can be displayed on the monitoring device 308. In addition, the data may, for example, be in a short message service (SMS) format or a multimedia message service (MMS). According to this embodiment, the signal may include, for example, text, voice, data and/or video messages involving medical instructions and/or notifications that alert or advise the subscriber 312 of a possible medical emergency. In another embodiment, the signal 316 may, for example, also cause a red or orange light on the monitoring device 308 to illuminate.

According to one embodiment of the present invention, the wireless network connectivity (depicted as signal 316) between the monitoring device 308 and the base station transceiver 304 and the wireless network connectivity (depicted as communications link 324) between the base station transceiver 304 and the personal computer 306 may be accomplished using radio frequencies (RF) such as, for example, IEEE 802.11 wireless LAN or Bluetooth technologies. The IEEE 802.11 standard defines the protocol for two types of networks: ad hoc and client/server networks. An ad hoc network may be a network in which communications are established between multiple stations in a given coverage area without the use of an access point or server. The standard specifies the etiquette that each station must observe so that all stations have fair access to the wireless media. It provides methods for arbitrating requests to use the media to ensure that throughput is maximized for all subscribers in the base service set. The client/server network uses an access point that controls the allocation of transmit time for all stations and allows mobile stations to roam from cell to cell. The access point is used to handle traffic from the mobile radio to the wired or wireless backbone of the client/server network. This arrangement allows for point coordination of all of the stations in the basic service area and ensures proper handling of the data traffic. The access point routes data between wireless stations or to and from the network server.

Bluetooth radio technology provides a universal bridge to existing data networks, a peripheral interface, and a mechanism to form small private ad hoc: groupings of connected devices away from fixed network infrastructures. Designed to operate in an RF environment, the Bluetooth radio uses a fast-acknowledgment and frequency-hopping scheme to make a robust link between a data network and a peripheral interface. In addition, Bluetooth radio modules may avoid interference from other signals by hopping to a new frequency after transmitting or receiving a data packet.

In another embodiment of the present invention, the server 78 may transmit a signal, via the network 310 and the wireless/wireline network 42, 44, to one or more communications devices 22a associated with the subscriber's home/workplace 314 and/or one or more communications devices 22b associated with an emergency contact(s) 322. In one embodiment, communications devices 22a and 22b may, for example, include a POTS telephone, as shown in FIG. 3, or, in other embodiments, communications devices 22a and 22b may include, for example, a personal computer, telecopier, wireless telephone, a personal digital assistant (PDA), and/or a pager.

In one embodiment, the wireless network 44 may communicate with the communications devices 22a and 22b according to an air-interface communication scheme 58 such as, for example, AMPS (ANSI-553), TDMA (IS-136), CDMA (IS-95), or GSM. In another embodiment, the wireline network 42 may communicate with communications devices 22a and 22b via communications links 20a and 20b, which may be conventional twisted pair loop circuits (i.e. Plain Old Telephone Service (POTS)), trunk circuits, such as T-1 trunk circuits, a Digital Subscriber Line (DSL), or an Integrated Services Digital Network (ISDN).

According to one embodiment of the present invention, the signal transmitted from the server 78 to the communications devices 20a and 20b may, for example, be in a short message service (SMS) format or a multimedia message service (MMS) format. According to this embodiment, the signal may include, for example, text, voice, data and/or video messages involving medical instructions and/or notifications that alert or advise the subscriber 312 and/or the emergency contact 322 of a possible medical emergency.

Figure 4A:
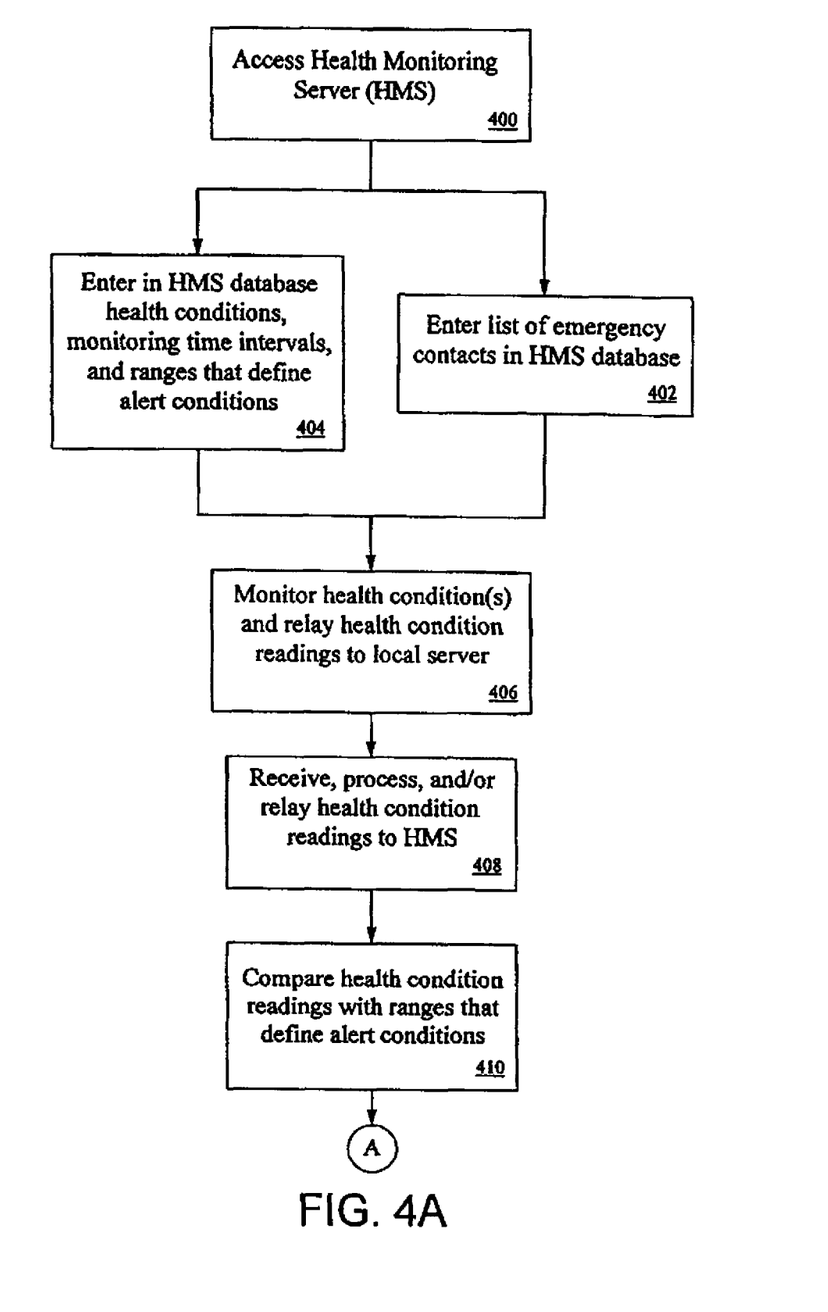
FIGS. 4a and 4b are flowcharts illustrating a process performed by the system shown in FIG. 3 according to one embodiment of the present invention.
Figure 4B:
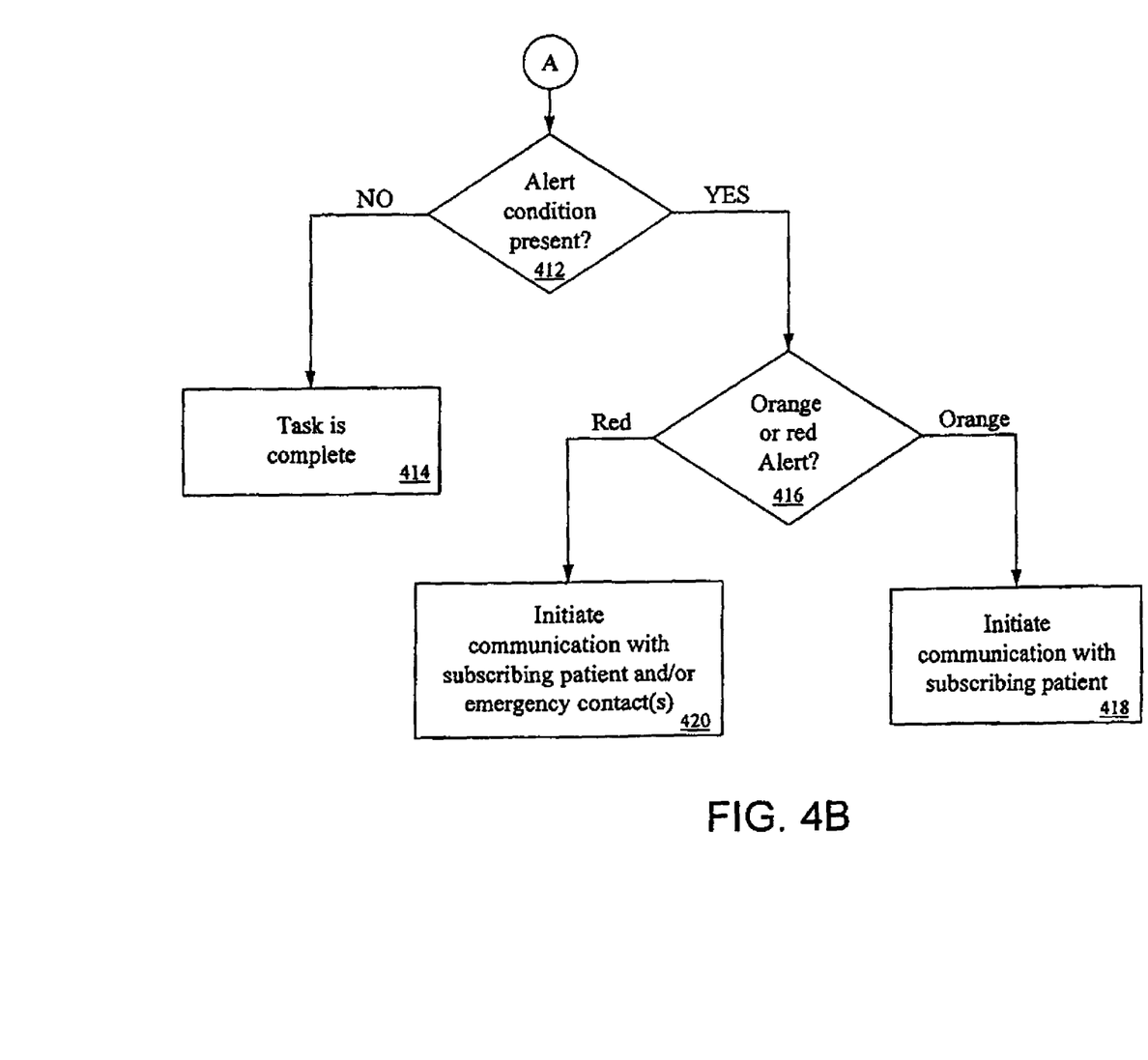

FIGS. 4a and 4b are flowcharts illustrating an embodiment of a process performed by the system 300 shown in FIG. 3. At step 400, the subscribing patient 312 and medical personnel, such as, for example, a physician or nurse, access the server 78. At step 402, the subscribing patient 312 enters into the database 80 of the server 78 a list of emergency contacts 322 and their associated contact information such as, for example, the email address or the telephone, facsimile, and/or pager number(s) of a doctor, ambulance service, neighbor, relative, the subscribing patient's 312 home/work place, etc.

In addition, medical personnel may, at step 404, enter into the database 80 the health condition(s) to be monitored and the time intervals in which to monitor them. Medical personnel may also enter ranges that define acceptable and unacceptable health levels as well as varying alert conditions that result from readings that do not fall within a predefined range. For example, the health condition of the subscribing patient 312 may be defined by measuring and recording a quantifiable parameter such as, for example, pulse, blood pressure, blood sugar, and cholesterol and then comparing the recorded measurement against the predefined range that a physician may establish for the subscribing patient 312. If the recorded measurement (i.e. the health condition reading) is within the predefined range, the patient's health may be considered satisfactory. In contrast, a health condition reading that falls outside the predefined range may trigger, for example, an orange or red alert (discussed below) that may cause a physician to further explore the nonconforming reading and ultimately prescribe medical treatment.

Once the subscribing patient 312 and medical personnel input the necessary information into the database 80, the monitoring device 308 may continually monitor the subscribing patient's 312 health condition identified by medical personnel in step 404 and relay, at defined time intervals, the health condition readings to the local server 302, as shown by step 406.

At step 408, the local server 302, may then receive, process and/or relay the health condition readings to the server 78. After receiving the health condition readings, the server 78, at step 410, may then compare the readings with the ranges that medical personnel defined in step 404. As shown at step 412, the server 78 then identifies if an alert condition exists. If the health condition reading is within the predefined range, no alert condition exists, and the task is complete at step 414. However, if the health condition reading is not within the predefined range, an alert condition exists and the process proceeds to step 416.

At step 416, the server 78 may further define the alert condition identified in step 412 to be, for example, an orange or red alert condition. In one embodiment of the present invention, an orange alert may occur if the health condition reading is slightly above or below the predefined range such that the reading falls within other ranges that medical personnel have defined to be an orange alert condition. In such case, the server 78 may, as shown by step 418, initiate a communication with the subscribing patient 312, via the health monitoring device 308 and/or the communications device 22a. According to one embodiment, the communication may, for example, involve illuminating an orange light on the monitoring device 308 and/or delivering one or more voice, data, text, or graphic messages to the monitoring device 308 and/or the communications device 22a that provide the subscribing patient 312 with medical instructions such as, for example, "you have been stressed, relax and take your prescribed medication."

In another embodiment of the present invention, a red alert may occur if the health condition reading is drastically above or below the predefined range such that the reading falls within other ranges that medical personnel have defined to be a red alert condition. In such case, the server 78 may, as shown by step 420, initiate a communication with or between the subscribing patient 312 and one or more emergency contacts 322, via the health monitoring device 308 and/or communications devices 22a and 22b. According to one embodiment, the communication may, for example, involve illuminating a red light on the monitoring device 308 and/or delivering one or more voice, data, text, or graphic messages to the monitoring device 308 and/or the communications devices 22a and 22b that may provide medical information and advice to the subscribing patient 312 and/or the emergency contact 322.

The various methods described hereinabove may be implemented on any type of suitable computer hardware, computer software, or combinations thereof. For example, the methods may be implemented in computer software using any suitable computer software language type such as, for example, C or C++ using, for example, conventional or object-oriented techniques. Such software may be stored on any type of suitable computer-readable medium or media such as, for example, a magnetic or optical storage medium.

While several embodiments of the invention have been described, it should be apparent, however, that various modifications, alterations and adaptations to those embodiments may occur to persons skilled in the art with the attainment of some or all of the advantages of the present invention. It is therefore intended to cover all such modifications, alterations and adaptations without departing from the scope and spirit of the present invention as defined by the appended claims.

The invention claimed is:

1. A method, comprising:
   receiving, by a mobile switching center, a health condition reading sent via a cellular network from a mobile device;
   querying, by the mobile switching center, the cellular network for an address assigned to the mobile device, the cellular network monitoring a personal health of a subscriber associated with the mobile device;
   identifying, by the mobile switching center, a medical range of data provided by the cellular network, the medical range of data identified based on the address assigned to the mobile device;
   determining, by the mobile switching center, that the health condition reading sent via the cellular network from the mobile device lies outside the medical range of data provided by the cellular network;
   generating, by the mobile switching center, a medical alert in response to the health condition reading lying outside the medical range of data provided by the cellular network; and
   sending, by the mobile switching center, the medical alert as a text message via the cellular network to the mobile device, the medical alert describing the health condition reading lying outside the medical range of data.

2. The method of claim 1, further comprising processing a call to the mobile device.

3. The method of claim 1, further comprising processing a call to an emergency number.

4. The method of claim 1, further comprising retrieving a medical instruction provided by the cellular network.

5. The method of claim 4, further comprising sending the medical instruction to the mobile device.

6. The method of claim 1, further comprising retrieving a contact address associated with the mobile device.

7. The method of claim 6, further comprising sending the medical alert to the contact address.

8. A system, comprising:
   a hardware processor; and
   a memory device, the memory device storing programming code, the programming code when executed causing the hardware processor to perform operations, the operations comprising:
   wirelessly receiving a health condition reading at a mobile switching center providing a health monitoring service to subscribers, the health condition reading sent via a cellular network from a mobile device requesting the health monitoring service;
   querying the cellular network for a network address assigned to the mobile device requesting the health monitoring service, the cellular network electronically associating the network address to a medical range of data;
   identifying the medical range of data that is electronically associated by the cellular network with the network address assigned to the mobile device requesting the health monitoring service;

determining, by the mobile switching center, that the health condition reading sent via the cellular network from the mobile device lies outside the medical range of data identified by the cellular network;

generating a medical alert by the mobile switching center in response to the health condition reading lying outside the medical range of data; and wirelessly transmitting the medical alert as a text message via the cellular network to the mobile device, the medical alert describing the health condition reading lying outside the medical range of data.

9. The system of claim 8, wherein the operations further comprise processing a call to the mobile device.

10. The system of claim 8, wherein the operations further comprise processing a call to an emergency number.

11. The system of claim 8, wherein the operations further comprise retrieving a medical instruction.

12. The system of claim 11, wherein the operations further comprise sending the medical instruction to the mobile device.

13. The system of claim 8, wherein the operations further comprise retrieving a contact address associated with the mobile device.

14. The system of claim 13, wherein the operations further comprise sending the medical alert to the contact address.

15. A method, comprising:

receiving, by a cellular mobile switching system, a health condition reading sent via a cellular network from a mobile device communicating with a health monitoring device via a residential network;

querying, by the cellular mobile switching system, the cellular network to identify a medical range of data, the cellular network providing medical ranges of data that are associated with addresses assigned to mobile devices;

determining, by the cellular mobile switching system, that the health condition reading sent via the cellular network from the mobile device lies outside the medical range of data;

generating, by the cellular mobile switching system, a medical alert describing the health condition reading lying outside the acceptable medical range of data; and sending, by the cellular mobile switching system, the medical alert as a text message via the cellular network to the mobile device, the medical alert describing the health condition reading lying outside the acceptable medical range of data.

16. The method of claim 15, further comprising retrieving a medical instruction.

17. The method of claim 16, further comprising wirelessly transmitting the medical instruction to the mobile device.

18. The method of claim 15, further comprising retrieving a contact address associated with the mobile device.

19. The method of claim 18, further comprising sending a notification to the contact address.

20. The method of claim 15, further comprising sending the medical alert to an emergency address.

* * * * *